(12) United States Patent
Iwai et al.

(10) Patent No.: US 11,504,443 B2
(45) Date of Patent: Nov. 22, 2022

(54) ODOR-MODULATING AGENT AND ODOR-MODULATING METHOD

(71) Applicants: YAMAMOTO PERFUMERY CO., LTD., Osaka (JP); SHIKIBO LTD., Osaka (JP); TOPPAN PRINTING CO., LTD., Tokyo (JP)

(72) Inventors: Ryota Iwai, Osaka (JP); Yutaka Tsujimoto, Osaka (JP); Yoshikuni Yamamoto, Osaka (JP); Takakazu Hige, Osaka (JP); Shoichiro Kudoh, Tokyo (JP); Toshiki Fujihara, Tokyo (JP)

(73) Assignees: YAMAMOTO PERFUMERY CO., LTD., Osaka (JP); SHIKIBO LTD., Osaka (JP); TOPPAN PRINTING CO., LTD., Tokyo (JP)

( * ) Notice: Subject to any disclaimer, the term of this patent is extended or adjusted under 35 U.S.C. 154(b) by 0 days.

(21) Appl. No.: 16/304,420

(22) PCT Filed: May 25, 2017

(86) PCT No.: PCT/JP2017/019592
§ 371 (c)(1),
(2) Date: Nov. 26, 2018

(87) PCT Pub. No.: WO2017/204305
PCT Pub. Date: Nov. 30, 2017

(65) Prior Publication Data
US 2019/0175777 A1    Jun. 13, 2019

(30) Foreign Application Priority Data

May 27, 2016   (JP) .............................. JP2016-106723

(51) Int. Cl.
*A61L 9/01*   (2006.01)
*A61L 9/14*   (2006.01)
*C11B 9/00*   (2006.01)

(52) U.S. Cl.
CPC .................. *A61L 9/01* (2013.01); *A61L 9/14* (2013.01); *C11B 9/00* (2013.01); *A61L 2209/21* (2013.01)

(58) Field of Classification Search
CPC .......... A61L 9/01; A61L 9/14; A61L 2209/00; C11B 9/00
See application file for complete search history.

(56) References Cited

U.S. PATENT DOCUMENTS

| 4,840,792 | A | * | 6/1989 | Joulain ..................... A61L 9/01 |
| | | | | 424/76.1 |
| 7,648,956 | B2 | | 1/2010 | Toki et al. |
| 7,786,331 | B2 | | 8/2010 | Toki et al. |
| 8,778,320 | B2 | | 7/2014 | Hiramoto et al. |
| 9,358,191 | B2 | | 6/2016 | Hiramoto et al. |
| 10,344,247 | B2 | | 7/2019 | Diaz Gomez et al. |
| 2004/0164029 | A1 | * | 8/2004 | Souter .................... A01N 59/00 |
| | | | | 210/764 |
| 2006/0165622 | A1 | | 7/2006 | Hiramoto et al. |
| 2007/0065394 | A1 | * | 3/2007 | Pinney .................... A61K 8/33 |
| | | | | 424/74 |
| 2009/0075859 | A1 | | 3/2009 | Toki et al. |
| 2009/0087401 | A1 | | 4/2009 | Hiramoto et al. |
| 2010/0010275 | A1 | | 1/2010 | Toki et al. |
| 2013/0136713 | A1 | | 5/2013 | Terada et al. |
| 2014/0162932 | A1 | | 6/2014 | Hatakeyama et al. |
| 2014/0271522 | A1 | | 9/2014 | Hiramoto et al. |
| 2015/0376546 | A1 | | 12/2015 | Diaz Gomez et al. |

FOREIGN PATENT DOCUMENTS

| CN | 101208416 | A | | 6/2008 |
| CN | 102171321 | A | | 8/2011 |
| CN | 103189076 | A | | 7/2013 |
| CN | 105219527 | A | | 1/2016 |
| EP | 1 884 251 | A1 | | 2/2008 |
| JP | 2002-336337 | A | | 11/2002 |
| JP | 2003-102819 | A | | 4/2003 |
| JP | 2003-113392 | A | | 4/2003 |
| JP | 2003102819 | A | * | 4/2003 |
| JP | 2003-190264 | A | | 7/2003 |
| JP | 2003190264 | A | * | 7/2003 |
| JP | 2004-167218 | A | | 6/2004 |
| JP | 2009-268754 | A | | 11/2009 |
| WO | 2013/018805 | A1 | | 2/2013 |
| WO | 2016/058710 | A1 | | 4/2016 |

OTHER PUBLICATIONS

Machine Translation of JP-2003102819-A. (Year: 2019).*
Machine translation of JP 2003190264 (A) provided by EPO and Google (Year: 2020).*
Google patent search_ethyl maltol and fecal and odor_Jan. 16, 2020 (Year: 2020).*
Google patent search_ethyl maltol and odor reduction_Jan. 13, 2020 (Year: 2020).*
Google patent search_vanillin in deodorizer_Jan. 13, 2020 (Year: 2020).*
C. S. Sell. On the Unpredictability of Odor. Angew. Chem. Int. Ed. 2006, 45, 6254-6261 (Year: 2006).*
Scifinder search for furans, tetrahydrofurans, pyrans and cyclopentanones; Jan. 30, 2021 (Year: 2021).*
International Search Report dated Jul. 11, 2017, issued in counterpad International Application No. PCT/JP2017/019592 (2 pages).

(Continued)

*Primary Examiner* — Michael P Cohen
(74) *Attorney, Agent, or Firm* — WHDA, LLP

(57) ABSTRACT

The present invention provides an odor-modulating agent that modulates malodors generated in daily living environments or industries to different odors so that harm caused by the malodors can be easily solved, and an odor-modulating method. Specifically, the present invention provides an odor-modulating agent comprising at least one oxygen-containing cyclic compound selected from the group consisting of furan compounds, pyran compounds, and cyclopentanone derivatives.

21 Claims, No Drawings

(56) References Cited

OTHER PUBLICATIONS

Notification of Reasons for Refusal dated Feb. 27, 2018, issued in counterpad Japanese Application No. 2016-106723, with English language machine translation (11 pages).
Extended Search Report dated Jan. 21, 2020, issued in counterpart EP Application No. 17802891.6 (7 pages).
Office Action dated Nov. 10, 2021, issued in the counterpart Chinese Application No. 201780032700.0 (14 pages; w/ English machine translation).
Shen, Y.D., "Introduction to Fine Chemicals", 1st ed., Beijing: Light Industry Press, pp. 42-44 (Aug. 1998) (cited in Chinese Office Action; w/ English translation).

* cited by examiner

ODOR-MODULATING AGENT AND ODOR-MODULATING METHOD

TECHNICAL FIELD

The present invention relates to an odor-modulating agent and an odor-modulating method.

BACKGROUND ART

Various malodors generated in daily living environments or industries, such as the farming industry, livestock industry, fishing industry, and manufacturing industry, have become problems.

In daily life, for example, there are various malodors including odors of rooms, odors in refrigerators, garbage odors, odors of shoe closets, body odors of humans or animals, odors of human or animal excreta, etc.

Patent Literature 1 (PTL 1), for example, discloses, as a means for improving these odors, a deodorizing composition comprising as an active ingredient a colored compound obtained by reacting polyphenol in an alkaline solvent in the coexistence of an oxygen molecule at a pH during the reaction of 6.5 or more. PTL 1 also discloses that the deodorizing composition is used for removing malodors generated in daily life.

However, such odors do not easily disappear, and cannot be sufficiently eliminated even by the use of the aforementioned deodorizer that intends to eliminate odors by getting rid of odors.

Further, in the fields of the livestock industry and the fishing industry, there are problems of malodors derived from excreta, etc., in livestock barns, such as cow barns, pig barns, and chicken farms, and fishy malodors from fishery facilities, such as fish markets and fish processing places.

In the livestock industry, for example, excreta of feeding cows, pigs, chickens, and other livestock are discharged from cow barns, pig barns, chicken farms, and like barns. Such excreta emit extremely strong malodors, which have become a significant source of pollution to neighbors. Moreover, malodors in barns have a bad influence on workers as well as livestock, and thus are significant problems for livestock farmers.

Additionally, in the fishing industry, there are fishy malodors derived from fish in fishery facilities, such as fish markets and fish processing places. Such odors cannot be easily eliminated, and have become a significant problem for workers.

As a means for improving these odors, Patent Literature 2 (PTL 2), for example, discloses a deodorizer comprising at least one acid selected from phosphoric acids, malic acids, citric acids, tartaric acids, and lactic acids. PTL 2 discloses a method for eliminating odors of livestock excreta etc., the method comprising bringing the deodorizer into contact with odors emitted from livestock excreta, such as cow dung, pig dung, and chicken dung, to thereby eliminate odors, and mixing the reaction solution obtained after the elimination of odors with the excreta for the treatment.

However, odors generated in the livestock industry, fishing industry, and like industries are malodors derived from livestock excreta etc. or characteristic fishy malodors. Such malodors cannot be entirely removed even by the use of the aforementioned deodorizer that intends to eliminate odors by getting rid of odors, and thus are problems.

Accordingly, development of the means for solving the problem of odors generated in daily living environments or industries has been desired.

CITATION LIST

Patent Literature

PTL 1: JP2004-167218A
PTL 2: JP2009-268754A

SUMMARY OF INVENTION

Technical Problem

An object of the present invention is to provide an odor-modulating agent that modulates malodors generated in daily living environments or industries to different odors so that harm caused by the malodors can be easily solved, and an odor-modulating method.

Solution to Problem

As a result of extensive research, the present inventors found the following. An odor-modulating agent that modulates malodors generated in daily living environments or industries to different odors, thereby allowing the subject to smell odors that are non-unpleasant, can sufficiently reduce an unpleasant feeling caused by these malodors. The present inventors also found that by spraying the odor-modulating agent in the air in daily living spaces or industrial facilities, including barns, such as cow barns, pig barns, and chicken farms, and fishery facilities, such as fish markets and fish processing places, malodors can be modulated to other odors, and an unpleasant feeling can be easily reduced. Thus, the present inventors solved the above problems, and accomplished the present invention.

Specifically, the present invention relates to the following odor-modulating agents and odor-modulating method.

1. An odor-modulating agent comprising at least one oxygen-containing cyclic compound selected from the group consisting of furan compounds, pyran compounds, and cyclopentanone derivatives.

2. The odor-modulating agent according to Item 1, wherein the oxygen-containing cyclic compound is contained in an amount of 10 to 20 mass % based on 100 mass % of the odor-modulating agent.

3. The odor-modulating agent according to Item 1 or 2, wherein the furan compound is at least one member selected from the group consisting of furaneol, furfural, 5-methylfurfural, furfuryl mercaptan, furfuryl alcohol, 2-propionylfuran, 2-ethylfuran, menthofuran, 2-methyl-3-furanthiol, 2-methyl-3-tetrahydrofuranthiol, 2-methyl-4,5-dihydro-3-furanthiol, 2-methylfuran, 2-methyltetrahydrofuran, 2-hexanoylfuran, 2-pentylfuran, 2-propylfuran, 2-(3-phenylpropyl)tetrahydrofuran, 2,3-dihydrobenzofuran, 2,4-dimethyl-4-phenyltetrahydrofuran, 2-furfuryl-5-methylfuran, 2-heptylfuran, 2-methylbenzofuran, 2-methyl-5-propionylfuran, 2-(5-ethenyl-5-methyltetrahydrofuran-2-yl)-propanal, 3-{[2-methyl-(2 or 4), 5-dihydro-3-furil]thio}-2-methyltetrahydrofuran-3-thiol, 2-ethenyl-5-isopropenyl-2-methyltetrahydrofuran, 5-methyl-2-furanmethanethiol, 6-methyl-2,3-dihydrothieno[2,3-c]furan, 2,5-dimethoxytetrahydrofuran, 3-acetyl-2,5-dimethylfuran, 2-acetyl-5-methylfuran, 2-acetylfuran, 2-butylfuran, 2,5-diethyltetrahydrofuran, difurfuryl disulfide, difurfuryl ether, difurfuryl sulfide, and 2,5-dimethyl-3-furanthiol.

4. The odor-modulating agent according to any one of Items 1 to 3, wherein the furan compound is contained in an amount of 0.8 to 5 mass % based on 100 mass % of the odor-modulating agent.

5. The odor-modulating agent according to any one of Items 1 to 4 wherein the pyran compound is at least one member selected from the group consisting of maltol, ethyl maltol, 4-acetoxy-3-pentyltetrahydropyran, 3,5-dihydroxy-6-methyl-2,3-dihydro-4(4H)-pyranon, 6-ethenyl-2,2,6-trimethyltetrahydropyran, 5-methyl-3-butyltetrahydropyran-4-yl acetate, octahydro-2H-1-benzopyran-2-one, 4-methyl-2-(2-methyl-1-propenyl)tetrahydropyran, theaspirane, vitispirane, (2S,4aR,8aS)-2,5,5,8a-tetramethyl-3,4,4a,5,6,8a-hexahydro-2H-1-benzopyran, 6-ethenyl-2,2,6-trimethyltetrahydro-3(4H)-pyranon, 6-hydroxydihydrotheaspirane, 6-acetoxydihydrotheaspirane, and 2,6-diethyl-5-isopropyl-2-methyltetrahydro-2H-pyran.

6. The odor-modulating agent according to any one of Items 1 to 5, wherein the pyran compound is contained in an amount of 5 to 20 mass % based on 100 mass % of the odor-modulating agent.

7. The odor-modulating agent according to any one of Items 1 to 6, wherein the cyclopentanone derivative is at least one member selected from the group consisting of cyclopentanone, cyclotene, cyclotene acetate, cyclotene propionate, cyclotene butyrate, cyclotene isobutyrate, 2-geranylcyclopentanone, 2-hexylcyclopentanone, 2-hexylidenecyclopentanone, 2-cyclopentylcyclopentanone, 2-amyl-2-cyclopentenone, 3-methyl-2-pentyl-2-cyclopentenone, 3-ethyl-2-hydroxy-2-cyclopentenone, 2-hydroxy-3,4-dimethyl-2-cyclopentenone, 2-methyl-3-(2-pentenyl)-2-cyclopentenone, 3-methyl-2-(cis-2-pentenyl)-2-cyclopentenone, 3-methyl-2-(trans-2-pentenyl)-2-cyclopentenone, 3-methyl-2-cyclopentenone, 3-ethyl-2-hydroxy-4-methyl-2-cyclopentenone, 2-hexyl-2-cyclopentenone, and 2,3-dimethyl-2-cyclopentenone.

8. The odor-modulating agent, according to any one of Items 1 to 7, wherein the cyclopentanone derivative is contained in an amount of 0.1 to 5 mass % based on 100 mass % of the odor-modulating agent.

9. The odor-modulating agent according to any one of Items 1 to 8, which further comprises a vanillin-based compound.

10. The odor-modulating agent according to Item 9, wherein the vanillin-based compound is at least one member selected from the group consisting of vanillin, ethyl vanillin, acetaldehyde ethyl vanillin acetal, vanillin acetate, ethyl vanillin isobutyrate, acetovanillone, ethyl vanillate, ethyl vanillin propylene glycol acetal, methyl vanilate, vanillic acid, vanillin isobutyrate, butyl vanilate, vanillin 2,3-butanediol acetal, and vanillin lactate.

11. The odor-modulating agent according to Item 9 or 10, wherein the vanillin-based compound is contained in an amount of 10 to 20 mass % based on 100 mass % of the odor-modulating agent.

12. The odor-modulating agent according to any one of Items 1 to 11, which further comprises pyridine.

13. The odor-modulating agent according to Item 12, wherein the pyridine is at least one member selected from the group consisting of 2-acetyl pyridine, 3-acetyl pyridine, 4-acetyl pyridine, 2-acetyl-1,4,5,6-tetrahydropyridine, 2-acetyl-4-isopropenylpyridine, 4-acetyl-2-isopropenylpyridine, 2-acetyl-4-isopropylpyridine, 3,5-dimethyl-4,5,6,7-tetrahydrothieno[3,2-c]pyridine, and 2-acetyl-3,4,5,6-tetrahydropyridine.

14. The odor-modulating agent according to any one of Items 1 to 13, which further comprises pyrazine.

15. The odor-modulating agent according to Item 14, wherein the pyrazine is at least one member selected from the group consisting of 2-methylthio-3-methylpyrazine, 2-methoxy-3-methylpyrazine, 2-ethyl-3(5/6)dimethylpyrazine, 2-ethyl-3-methylpyrazine, 2-methoxy-5-methylpyrazine, 2-acetyl-3, (5/6)-dimethylpyrazine, 2-acetyl-3-ethylpyrazine, 2-acetyl-3-methylpyrazine, acetylpyrazine, 2-(furfurylthio)-(3/5/6)-methylpyrazine, 2-methyl-(5/6)-(methylthio)pyrazine, 2-ethyl-3-(methylthio)pyrazine 2-isopropyl-3-(methylthio)pyrazine, 2-sec-butyl-3-methoxypyrazine, 2-ethoxy-(3/5/6)-methylpyrazine, 2-ethoxy-3-ethylpyrazine, 2-ethoxy-3-isopropylpyrazine, 2-ethyl-3-methoxypyrazine, 2-hexyl-3-methoxypyrazine, 2-isobutyl-3-methoxypyrazine, 2-isopropoxy-3-methylpyrazine, 2-isopropyl-(3/5/6)-methoxypyrazine, 2-methoxy-(5/6)-methylpyrazine, 2-methoxy-3,5-dimethylpyrazine, 2-isopropyl-3-methoxypyrazine, methoxypyrazine, 2-methyl-6-propoxypyrazine, 2-ethoxy-(5/6)-methylpyrazine, 2-ethoxy-3-ethylpyrazine, 2-ethoxy-3-isopropylpyrazine, 2-hexyl-3-methoxypyrazine, and 2-(hydroxymethyl)-5-methylpyrazine.

16. The odor-modulating agent according to any one of Items 1 to 15 for use in livestock raising or fishing processing.

17. An odor-modulating method comprising spraying in the air an odor-modulating agent comprising at least one oxygen-containing cyclic compound selected from the group consisting of furan compounds, pyran compounds, and cyclopentanone derivatives.

Advantageous Effects of Invention

The odor-modulating agent of the present invention can modulate malodors generated in daily living environments or industries to different odors, thereby allowing the subject to smell other odors that are non-unpleasant, and can reduce an unpleasant feeling caused by these malodors. Further, the odor-modulating method of the present invention can modulate malodors to other odors by spraying the odor-modulating agent in the air in daily living spaces or industrial facilities including barns, such as cow barns, pig barns, and chicken farms, and fishery facilities, such as fish markets and fish processing places, and can easily reduce an unpleasant feeling caused by these malodors.

DESCRIPTION OF EMBODIMENTS

The odor-modulating agent and the odor-modulating method according to the present invention are explained in detail below.

1. Odor-Modulating Agent

The odor-modulating agent of the present invention comprises at least one oxygen-containing cyclic compound selected from the group consisting of furan compounds, pyran compounds, and cyclopentanone derivatives.

Furan Compound

The furan compound is not limited as long as it is an oxygen-containing cyclic compound having a furan skeleton, i.e., a five-membered ring consisting of four carbon atoms and one oxygen atom. Examples of furan compounds include furaneol, furfural, 5-methylfurfural, furfuryl mercaptan, furfuryl alcohol, 2-propionylfuran, 2-ethylfuran, menthofuran, 2-methyl-3-furanthiol, 2-methyl-3-tetrahydrofuranthiol, 2-methyl-4,5-dihydro-3-furanthiol, 2-methylfuran, 2-methyltetrahydrofuran, 2-hexanoylfuran, 2-pentylfuran, 2-propylfuran, 2-(3-phenylpropyl)tetrahydrofuran, 2,3-dihydrobenzofuran, 2,4-dimethyl-4-phenyltetrahydrofuran, 2-furfuryl-5-methylfuran, 2-heptylfuran, 2-methylbenzofuran, 2-methyl-5-propionylfuran, 2-(5-ethenyl-5-methyltetrahydrofuran-2-yl) -propanal, 3-{[2-methyl-(2or 4), 5-dihydro-3-furil]thio}-2-methyltetrahydrofuran-3-thiol, 2-ethenyl-5-isopropenyl-2-methyltetrahydrofuran, 5-methyl-2-furanmethanethiol, 6-methyl-2,3-dihydrothieno[2,3-c]furan, 2,5-dimethoxytetrahydrofuran, 3-acetyl-2,5-dimethylfuran, 2-acetyl-5-methylfuran, 2-acetylfuran, 2-butylfuran, 2,5-diethyltetrahydrofuran, difurfuryl disulfide, difurfuryl ether, difurfuryl sulfide, and 2,5-dimethyl-3-furanthiol. Of these, furaneol, 5-methylfurfural, and furfuryl mercaptan are preferable.

The amount of the furan compound is preferably 0.5 to 10 mass %, more preferably 0.8 to 5 mass %, and even more preferably 0.8 to 3 mass %, particularly preferably 0.8 to 1.5 mass %, and most preferably 0.9 to 1.2 mass % based on 100 mass % of the odor-modulating agent. By setting the amount of the furan compound to the above range, the odor-modulating agent can more easily modulate malodors generated in daily living environments or industries to other odors, and can more efficiently reduce an unpleasant feeling caused by these odors.

Such furan compounds can be used alone or in a mixture of two or more.

Pyran Compound

The pyran compound is not limited as long as it is an oxygen-containing cyclic compound having a pyran skeleton, specifically having a 6-membered ether compound consisting of 5 carbon atoms and 1 oxygen atom as the skeleton. Examples of pyran compounds include maltol, ethyl maltol, 4-acetoxy-3-pentyltetrahydropyran, 3,5-dihydroxy-6-methyl-2,3-dihydro-4(4H)-pyranon, 6-ethenyl-2,2,6-trimethyltetrahydropyran, 5-methyl-3-butyltetrahydropyran-4-yl acetate, octahydro-2H-1-benzopyran-2-one, 4-methyl-2-(2-methyl-1-propenyl)tetrahydropyran, theaspirane, vitispirane, (2S,4aR,8aS)-2,5,5,8a-tetramethyl-3,4,4a,5,6,8a-hexahydro-2H-1-benzopyran, 6-ethenyl-2,2,6-trimethyltetrahydro-3(4H)-pyranon, 6-hydroxydihydrotheaspirane, 6-acetoxydihydrotheaspirane, and 2,6-diethyl-5-isopropyl-2-methyltetrahydro-2H-pyran. Of these, ethyl maltol is preferable.

The amount of the pyran compound is preferably 5 to 20 mass %, more preferably 5 to 15 mass %, even more preferably 8 to 15 mass %, and particularly preferably 8 to 12 mass % based on 100 mass % of the odor-modulating agent. By setting the amount of the pyran compound to the above range, the odor-modulating agent can more easily modulate malodors generated in daily living environments or industries to other odors, and can more efficiently reduce an unpleasant feeling caused by these odors.

Such pyran compounds can be used alone or in a mixture of two or more.

Cyclopentanone Derivative

The cyclopentanone derivative is not limited as long as it is an oxygen-containing cyclic compound having an oxygen atom and a cyclopentane skeleton, i.e., a 5-membered ring consisting of five carbon atoms. Examples of cyclopentanone derivatives include cyclopentanone, cyclotene, cyclotene acetate, cyclotene propionate, cyclotene butyrate, cyclotene isobutyrate, 2-geranylcyclopentanone, 2-hexylcyclopentanone, 2-hexylidenecyclopentanone, 2-cyclopentylcyclopentanone, 2-amyl-2-cyclopentenone, 3-methyl-2-pentyl-2-cyclopentenone, 3-ethyl-2-hydroxy-2-cyclopentenone, 2-hydroxy-3,4-dimethyl-2-cyclopentenone, 2-methyl-3-(2-pentenyl)-2-cyclopentenone, 3-methyl-2-(cis-2-pentenyl)-2-cyclopentenone, 3-methyl-2-(trans-2-pentenyl)-2-cyclopentenone, 3-methyl-2-cyclopentenone, 3-ethyl-2-hydroxy-4-methyl-2-cyclopentenone, 2-hexyl-2-cyclopentenone, and 2,3-dimethyl-2-cyclopentenone. Of these, cyclotene is preferable.

The amount of the cyclopentanone derivative is preferably 0.1 to 5 mass %, and more preferably 0.5 to 3 mass % based on 100 mass % of the odor-modulating agent. By setting the amount of the pyran compound to the above range, the odor-modulating agent can more easily modulate malodors generated in daily living environments or industries to other odors, and can more efficiently reduce an unpleasant feeling caused by these odors.

Such cyclopentanone derivatives can be used alone or in a mixture of two or more.

The amount of the oxygen-containing cyclic compound in the odor-modulating agent, specifically, the sum of the amounts of the furan compound, pyran compound, and the cyclopentanone derivative is preferably 5 to 25 mass %, more preferably 5 to 20 mass %, even more preferably 10 to 20 mass %, and particularly preferably 10 to 15 mass % based on 100 mass % of the odor-modulating agent. By setting the amount of the oxygen-containing cyclic compound to the above range, the odor-modulating agent can more easily modulate malodors generated in daily living environments or industries to other odors, and can more efficiently reduce an unpleasant feeling caused by these odors.

The content ratio of the furan compound and pyran compound in the odor-modulating agent is preferably such that the molar ratio of the furan compound:the pyran compound=1:2 to 1:5, and more preferably 1:3 to 1:4. By setting the content ratio of the furan compound and pyran compound to the above range, the odor-modulating agent can more easily modulate-malodors generated in daily living environments or industries to other odors, and can more efficiently reduce an unpleasant feeling caused by these odors.

Vanillin-Based Compound

It is preferable that the odor-modulating agent of the present invention further comprises a vanillin-based compound. By containing a vanillin-based compound in the odor-modulating agent, more excellent odor-modulating effects can be obtained, and an unpleasant feeling caused by malodors generated in daily living environments or industries can be more efficiently reduced.

The vanillin-based compound is not limited as long as it is a compound having a vanillin skeleton. Examples of vanillin-based compounds include vanillin, ethyl vanillin, acetaldehyde ethyl vanillin acetal, vanillin acetate, ethyl vanillin isobutyrate, acetovanillone, ethyl vanillate, ethyl vanillin propylene glycol acetal, methyl vanilate, vanillic acid, vanillin isobutyrate, butyl vanilate, vanillin 2,3-butanediol acetal, and vanillin lactate. Of these, vanillin and ethyl vanillin are preferable.

The amount of the vanillin-based compound is preferably 5 to 25 mass %, more preferably 5 to 20 mass %, even more preferably 10 to 20 mass %, and particularly preferably 10 to 15 mass % based on 100 mass % of the odor-modulating agent. By setting the amount of the vanillin-based compound to the above range, the odor-modulating agent can more easily modulate malodors generated in daily living environments or industries to other odors, and can more efficiently reduce an unpleasant feeling caused by these odors.

Such vanillin-based compounds can be used alone or in a mixture of two or more.

Pyridine

It is preferable that the odor-modulating agent of the present invention further comprises pyridine. By containing pyridine in the odor-modulating agent, more excellent odor-modulating effects can be obtained, and an unpleasant feeling caused by malodors generated in daily living environments or industries can be more efficiently reduced.

The pyridine is not limited as long as it is a nitrogen-containing heterocyclic aromatic compound having a pyridine skeleton, specifically having a pyridine with a 6-membered ring structure consisting of 5 carbon atoms and 1 nitrogen atom as the skeleton. Examples of pyridines include 2-acetyl pyridine, 3-acetyl pyridine, 4-acetyl pyridine, 2-acetyl-1,4,5,6-tetrahydropyridine, 2-acetyl-4-isopropenylpyridine, 4-acetyl-2-isopropenylpyridine, 2-acetyl-4-isopropylpyridine, 3,5-dimethyl-4,5,6,7-tetrahydrothieno[3,2-c] pyridine, and 2-acetyl-3,4,5,6-tetrahydropyridine. Of these, 2-acetyl pyridine is preferable.

The amount of the pyridine is preferably 0.05 to 0.3 mass %, and more preferably 0.1 to 0.2 mass % based on 100 mass % of the odor-modulating agent. By setting the amount of the pyridine to the above range, the odor-modulating agent can more easily modulate malodors generated in daily living environments or industries to other odors, and can more efficiently reduce an unpleasant feeling caused by these odors.

Such pyridines can be used alone or in a mixture of two or more.

Pyrazine

It is preferable that the odor-modulating agent of the present invention further comprises pyrazine. By containing pyrazine in the odor-modulating agent, more excellent odor-modulating effects can be obtained, and an unpleasant feeling caused by malodors generated in daily living environments or industries can be more efficiently reduced.

The pyrazine is not limited as long as it is a nitrogen-containing heterocyclic aromatic compound having a pyrazine skeleton, specifically having a pyrazine, which is a compound with a 6-membered ring structure consisting of 4 carbon atoms and 2 nitrogen atoms, as the skeleton. Examples of pyrazines include 2-methylthio-3-methylpyrazine, 2-methoxy-3-methylpyrazine, 2-ethyl-3(5/6)dimethylpyrazine, 2-ethyl-3-methylpyrazine, 2-methoxy-5-methylpyrazine, 2-acetyl-3, (5/6)-dimethylpyrazine, 2-acetyl-3-ethylpyrazine, 2-acetyl-3-methylpyrazine, acetylpyrazine, 2-(furfurylthio)-(3/5/6)-methylpyrazine, 2-methyl-(5/6)-(methylthio)pyrazine, 2-ethyl-3-(methylthio)pyrazine 2-isopropyl-3-(methylthio)pyrazine, 2-sec-butyl-3-methoxypyrazine, 2-ethoxy-(3/5/6)-methylpyrazine, 2-ethoxy-3-ethylpyrazine, 2-ethoxy-3-isopropylpyrazine, 2-ethyl-3-methoxypyrazine, 2-hexyl-3-methoxypyrazine, 2-isobutyl-3-methoxypyrazine, 2-isopropoxy-3-methylpyrazine, 2-isopropyl-(3/5/6)-methoxypyrazine, 2-methoxy-(5/6)-methylpyrazine, 2-methoxy-3,5-dimethylpyrazine, 2-isopropyl-3-methoxypyrazine, methoxypyrazine, 2-methyl-6-propoxypyrazine, 2-ethoxy-(5/6)-methylpyrazine, 2-ethoxy-3-ethylpyrazine, 2-ethoxy-3-isopropylpyrazine, 2-hexyl-3-methoxypyrazine, and 2-(hydroxymethyl)-5-methylpyrazine. Of these, 2-methylthio-3-methyl pyrazine is preferable.

The amount of the pyrazine is preferably 0.1 to 0.5 mass %, more preferably 0.2 to 0.5 mass %, even more preferably 0.2 to 0.4 mass %, and particularly preferably 0.3 to 0.4 mass % based on 100 mass % of the odor-modulating agent. By setting the amount of the pyrazine to the above range, the odor-modulating agent can more easily modulate malodors generated in daily living environments or industries to other odors, and can more efficiently reduce an unpleasant feeling caused by these odors.

Such pyrazines can be used alone or in a mixture of two or more.

Other Additives

As long as the effects of the present invention are not impaired, the odor-modulating agent of the present invention may contain other additives. Examples of other additives include organic acids other than the furan compounds, pyran compounds, vanillin-based compounds, pyridines, and pyrazines mentioned above, ester-based compounds, aldehyde-based compounds, ketone-based compounds, etc.

The sum of the amounts of the other additives in the odor-modulating agent is preferably 30 mass % or less, more preferably 20 mass % or less, even more preferably 10 mass % or less, and particularly preferably 5 mass % or less based on 100 mass % of the odor-modulating agent. By setting the sum of the amounts of the other additives to the above range, the odor-modulating agent can more easily modulate malodors generated in daily living environments or industries to other odors, and can more efficiently reduce an unpleasant feeling caused by these odors.

Solvent

It is preferable that each component of the odor-modulating agent of the present invention is dispersed in a solvent. Because the components are dispersed in a solvent, the odor-modulating agent can be easily sprayed in the air in daily living spaces or industrial facilities, including barns, such as cow barns, pig barns, and chicken farms, and fishery facilities, such as fish markets and fish processing places.

As a solvent, water and solvents can be used. The solvent is not limited, and examples include alcohol, ether, ketone, ester, etc. Of these, alcohol is preferable because of its appropriate volatility and low harmful effects on humans or livestock when the odor-modulating agent is sprayed in the air.

The alcohol is not limited, and examples include mono-alcohol, or diol, triol, and like polyols. As the alcohol, those having 2 to 4 carbon atoms can be suitably used. The number of carbons of the alcohols is preferably 2 to 3.

Specific examples of alcohols include ethanol, propylene glycol, glycerin, etc. Ethanol and propylene glycol are preferable because of their appropriate volatility and low harmful effects on humans or livestock when the odor-modulating agent is sprayed.

Such solvents can be used alone or in a mixture of two or more.

The amount of the solvent is preferably 20 to 30 mass %, more preferably 30 to 30 mass %, even more preferably 40 to 80 mass %, and particularly preferably 50 to 80 mass % based on 100 mass % of the odor-modulating agent. By setting the amount of the solvent to the above range, the odor-modulating agent can be easily sprayed in the air, and shows appropriate volatility and retainability when being sprayed in the air.

When water and a solvent are mixed for use as a solvent, the content ratio of water and the solvent is such that the mass ratio of water:solvent is preferably 2:98 to 10:90, and more preferably 10:90 to 20:80. By setting the content ratio of water and the solvent to the above range, the odor-modulating agent shows appropriate volatility and can reduce harmful effects on humans or livestock when being sprayed in the air.

The odor-modulating agent of the present invention can be advantageously used at places with malodors. In particular, the odor-modulating agent is preferably used as an odor-modulating agent for livestock raising or fish processing. By using the odor-modulating agent for livestock raising or fish processing, the odor-modulating agent can modulate malodors derived from livestock excreta etc. or characteristic fishery malodors generated in the livestock industry or fishing industry to different odors, thus allowing the subject to smell other odors that are non-unpleasant. Accordingly, an unpleasant feeling caused by these odors can be reduced, and the effects of the odor-modulating agent of the present invention can be more significantly exhibited.

2. Odor-Modulating Method

The present invention also provides an odor-modulating method comprising spraying in the air an odor-modulating agent comprising at least one oxygen-containing cyclic compound selected from the group consisting of furan compounds, pyran compounds, and cyclopentanone derivatives.

As the odor-modulating agent to be sprayed in the odor-modulating method of the present invention, the odor-modulating agent mentioned above can be used.

The spraying method is not limited as long as the odor-modulating agent can be sprayed in the air. Examples of the spraying method include a method of spray atomization, a method of spraying the odor-modulating agent together with manure using a manure spreader, a method of scattering the odor-modulating agent by wind, etc.

The temperature of the odor-modulating agent during spraying is not limited and is preferably 10 to 25° C., and more preferably 15 to 20° C. By spraying the odor-modulating agent at the temperature in the above range, the odor-modulating agent can be more efficiently sprayed in a wider range.

When the method of spray atomization is used for spraying, the pressure during spraying is preferably 0.2 to 0.6 MPa, and more preferably 0.3 to 0.5 MPa. By spraying the odor-modulating agent at a pressure in the above range, the odor-modulating agent can be more efficiently sprayed in a wider range.

The place where the odor-modulating agent is sprayed is not limited. The odor-modulating agent can be sprayed in the air in daily living spaces or industrial facilities, including barns, such as cow barns, pig barns, and chicken farms, and fishery facilities, such as fish markets and fish processing places. By spraying the odor-modulating agent in the air in such places, malodors can be modulated to other odors to thereby easily reduce an unpleasant feeling. In the odor-modulating method of the present invention, it is preferable that the odor-modulating agent is sprayed in barns, such as cow barns, pig barns, and chicken farms, and fishery facilities, such as fish markets and fish processing places. By spraying the odor-modulating agent in the air in such places, malodors derived from dung etc. or characteristic fishery malodors can be modulated to other odors to thereby easily reduce an unpleasant feeling caused by these malodors. Thus, the effects of the odor-modulating method of the present invention can be more significantly exhibited.

EXAMPLES

The present invention is detailed below with reference to Examples and Comparative Examples. However, the present invention is not limited thereto.

Preparation of Odor-Modulating Agent

Starting materials of an odor-modulating agent shown in Table 1 were introduced into a mixing tank, followed by mixing and stirring to prepare an odor-modulating agent. More specifically, a solvent having a formulation shown in Table 1 was introduced into a mixing tank equipped with a heating device, then other starting materials were sequentially added, and the mixture was stirred at 20° C. for 30 minutes, thus preparing an odor-modulating agent.

Evaluation

The following evaluation was performed using odor-modulating agents of Examples and Comparative Examples prepared as above. Specifically, each of the odor-modulating agents of the Examples and Comparative Examples was mixed in a manner such that the mass ratio of propylene glycol (PG):water:odor-modulating agent=45:59:5, thus preparing dilutions.

Subsequently, 0.5 g of cow dung was put in a plastic cap (lid) with an inner diameter of 2 cm. Filter paper No. 2 was put on the bottom of a sterilized petri dish for examining bacteria, and the cap was placed on the center of the filter paper. 0.2 g of a dilution was added dropwise in a circular manner to the filter paper around the cap, thus preparing a sample. A blank to which a dilution was not added dropwise was also prepared.

Subsequently, the sample and the blank were each covered with a petri dish, and allowed to stand at room temperature (20° C.) for 10 minutes. Thereafter, the cover was opened, and subjects smelled the odor 10 cm above the center of the petri dish. Sensory evaluation was thus performed by comparing the odor of the blank according to the following evaluation criteria. The above examination was performed by 8 subjects. The evaluation was performed using a score obtained by multiplying the number of subjects who gave each rating by an allocated point according to the following evaluation criteria.

(1) Whether or not the subject felt the smell of cow dung.

The subject did not feel the smell of cow dung at all (3 points).

The subject did not feel the smell of cow dung (2 points).

The subject felt a slight smell of cow dung (1 point).

The subject felt the smell of cow dung (0 points).

(2) Whether or not the subject felt that the smell was changed from the blank.

The subject felt that the smell was changed from the blank (3 points).

The subject felt that the smell was slightly changed from the blank (2 points).

The subject felt that the smell was not changed so much from the blank (1 point).
The subject felt that the smell was not changed at all from the blank (0 points).
(3) Whether or not the subject felt that the smell was good.
The subject felt that the smell was good (3 points).
The subject felt that the smell was slightly good (2 points).
The subject felt that the smell was not so good (1 point).
The subject felt that the smell was not good at all (0 points).
The same examinations were conducted for pig dung and chicken dung. The same sensory evaluation was performed.
Table 1 shows the results.

The invention claimed is:
1. An odor-modulating agent comprising
an oxygen-containing cyclic compound comprising at least one furan compound and at least one pyran compound,
wherein
the oxygen-containing cyclic compound is contained in an amount of 10 to 25 mass % based on 100 mass % of the odor-modulating agent,
the at least one furan compound is contained in an amount of 3 mass % or less based on 100 mass % of the odor-modulating agent,
the at least one furan compound comprises furaneol, 5-methylfurfural, and furfuryl mercaptan, and
the at least one pyran compound comprises ethyl maltol.

TABLE 1

| | (Mass %) | Example 1 | Example 2 | Comparative Example 1 | Comparative Example 2 |
|---|---|---|---|---|---|
| Vanillin-based compound | Vanillin | 0.92 | 0.35 | — | — |
| | Ethyl vanillin | 10.00 | 10.00 | — | — |
| Cyclopentanone derivative | Cyclotene | 1.00 | 1.00 | — | — |
| Furan compound | Furaneol | 0.45 | 0.45 | — | — |
| | 5-Methylfurfural | 0.50 | 0.50 | — | — |
| | Furfuryl mercaptan | 0.03 | 0.03 | — | — |
| | Furfural | 0.09 | — | — | — |
| | Furfuryl alcohol | 0.43 | — | — | — |
| Pyran compound | Ethyl maltol | 10.00 | 10.00 | — | — |
| Pyridine | 2-Acetyl pyridine | 0.20 | 0.20 | — | — |
| Pyrazine | 2-Methylthio-3-methylpyrazine | 0.10 | 0.10 | 0.10 | — |
| | 2-Methoxy-3-methylpyrazine, | 0.17 | 0.10 | 0.17 | — |
| | 2-Ethyl-3(5/6)dimethylpyrazine, | 0.10 | 0.10 | 0.10 | — |
| | 2-Ethyl-3-methylpyrazine, | 0.03 | 0.03 | 0.03 | — |
| | 2-Methoxy-5-methylpyrazine | 0.03 | — | 0.03 | — |
| | 2-Acetylpyrazine | — | — | — | 24.32 |
| Others | Organic acid | 0.02 | — | — | — |
| | Ester-based compound | 0.10 | — | — | — |
| | Aldehyde-based compound | 0.05 | — | — | — |
| | Ketone-based compound | 0.09 | — | — | — |
| Solvent | Ethanol | 44.91 | 44.80 | 44.91 | 44.91 |
| | Propylene glycol | 18.32 | 18.32 | 18.32 | 18.32 |
| | Benzil alcohol | 6.17 | — | 6.17 | 6.17 |
| | Triethyl citrate | 4.43 | — | 4.43 | 4.43 |
| | Water | 1.85 | 14.02 | 25.73 | 1.85 |
| | Total | 100.00 | 100.00 | 100.00 | 100.00 |
| Cow dung (point) | Whether the subject felt the smell of cow dung | 13 | 16 | 8 | 7 |
| | Whether the subject felt that the smell was changed from the blank. | 7 | 11 | 5 | 5 |
| | Whether the subject felt that the smell was good | 10 | 14 | 5 | 4 |
| Pig dung (point) | Whether the subject felt the smell of pig dung | 11 | 13 | 5 | 7 |
| | Whether the subject felt that the smell was changed from the blank. | 8 | 10 | 2 | 5 |
| | Whether the subject felt that the smell was good | 7 | 11 | 4 | 5 |
| Chicken dung (point) | Whether the subject felt the smell of chicken dung | 12 | 12 | 8 | 7 |
| | Whether the subject felt that the smell was changed from the blank. | 9 | 13 | 8 | 7 |
| | Whether the subject felt that the smell was good | 9 | 10 | 5 | 3 |

2. The odor-modulating agent according to claim 1, wherein the oxygen-containing cyclic compound is contained in an amount of 10 to 20 mass % based on 100 mass % of the odor-modulating agent.

3. The odor-modulating agent according to claim 1, wherein the furan compound is contained in an amount of 0.8 to 3 mass % based on 100 mass % of the odor-modulating agent.

4. The odor-modulating agent according to claim 1, wherein the pyran compound is contained in an amount of 5 to 20 mass % based on 100 mass % of the odor-modulating agent.

5. The odor-modulating agent according to claim 1, wherein the oxygen-containing cyclic compound further comprises a cyclopentanone derivative that is at least one member selected from the group consisting of cyclopentanone, cyclotene, cyclotene acetate, cyclotene propionate, cyclotene butyrate, cyclotene isobutyrate, 2-geranylcyclopentanone, 2-hexylcyclopentanone, 2-hexylidenecyclopentanone, 2-cyclopentylcyclopentanone, 2-amyl-2-cyclopentenone, 3-methyl-2-pentyl-2-cyclopentenone, 3-ethyl-2-hydroxy-2-cyclopentenone, 2-hydroxy-3,4-dimethyl-2-cyclopentenone, 2-methyl-3-(2-pentenyl)-2-cyclopentenone, 3-methyl-2-(cis-2-pentenyl)-2-cyclopentenone, 3-methyl-2-(trans-2-pentenyl)-2-cyclopentenone, 3-methyl-2-cyclopentenone, 3-ethyl-2-hydroxy-4-methyl-2-cyclopentenone, 2-hexyl-2-cyclopentenone, and 2,3-dimethyl-2-cyclopentenone.

6. The odor-modulating agent according to claim 5, wherein the cyclopentanone derivative is contained in an amount of 0.1 to 5 mass % based on 100 mass % of the odor-modulating agent.

7. The odor-modulating agent according to claim 1, which further comprises a vanillin-based compound.

8. The odor-modulating agent according to claim 7, wherein the vanillin-based compound is at least one member selected from the group consisting of vanillin, ethyl vanillin, acetaldehyde ethyl vanillin acetal, vanillin acetate, ethyl vanillin isobutyrate, acetovanillone, ethyl vanillate, ethyl vanillin propylene glycol acetal, methyl vanilate, vanillic acid, vanillin isobutyrate, butyl vanilate, vanillin 2,3-butanediol acetal, and vanillin lactate.

9. The odor-modulating agent according to claim 7, wherein the vanillin-based compound is contained in an amount of 10 to 20 mass % based on 100 mass % of the odor-modulating agent.

10. The odor-modulating agent according to claim 1, which further comprises pyridine.

11. The odor-modulating agent according to claim 10, wherein the pyridine is at least one member selected from the group consisting of 2-acetyl pyridine, 3-acetyl pyridine, 4-acetyl pyridine, 2-acetyl-1,4,5,6-tetrahydropyridine, 2-acetyl-4-isopropenylpyridine, 4-acetyl-2-isopropenylpyridine, 2-acetyl-4-isopropylpyridine, 3,5-dimethyl-4,5, 6,7-tetrahydrothieno [3,2-c] pyridine, and 2-acetyl-3,4,5,6-tetrahydropyridine.

12. The odor-modulating agent according to claim 1, which further comprises pyrazine.

13. The odor-modulating agent according to claim 12, wherein the pyrazine is at least one member selected from the group consisting of 2-methylthio-3-methylpyrazine, 2-methoxy-3-methylpyrazine, 2-ethyl-3 (5/6)dimethylpyrazine, 2-ethyl-3-methylpyrazine, 2-methoxy-5-methylpyrazine, 2-acetyl-3,(5/6)-dimethylpyrazine, 2-acetyl-3-ethylpyrazine, 2-acetyl-3-methylpyrazine, acetylpyrazine, 2-(furfurylthio)-(3/5/6)-methylpyrazine, 2-methyl-(5/6)-(methylthio)pyrazine, 2-ethyl-3-(methylthio)pyrazine 2-isopropyl-3-(methylthio)pyrazine, 2-sec-butyl-3-methoxypyrazine, 2-ethoxy-(3/5/6)-methylpyrazine, 2-ethoxy-3-ethylpyrazine, 2-ethoxy-3-isopropylpyrazine, 2-ethyl-3-methoxypyrazine, 2-hexyl-3-methoxypyrazine, 2-isobutyl-3-methoxypyrazine, 2-isopropoxy-3-methylpyrazine, 2-isopropyl-(3/5/6)-methoxypyrazine, 2-methoxy-(5/6)-methylpyrazine, 2-methoxy-3,5-dimethylpyrazine, 2-isopropyl-3-methoxypyrazine, methoxypyrazine, 2-methyl-6-propoxypyrazine, 2-ethoxy-(5/6)-methylpyrazine, 2-ethoxy-3-ethylpyrazine, 2-ethoxy-3-isopropylpyrazine, 2-hexyl-3-methoxypyrazine, and 2-(hydroxymethyl)-5-methylpyrazine.

14. The odor-modulating agent according to claim 1 for use in livestock raising or fishing processing.

15. The odor-modulating agent according to claim 1, wherein the oxygen-containing cyclic compound further comprises at least one cyclopentanone derivative.

16. The odor-modulating agent according to claim 15, wherein the furan compound is contained in an amount of 0.8 to 3 mass % based on 100 mass % of the odor-modulating agent;
wherein the pyran compound is contained in an amount of 5 to 20 mass % based on 100 mass % of the odor-modulating agent; and
wherein the cyclopentanone derivative is contained in an amount of 0.1 to 5 mass % based on 100 mass % of the odor-modulating agent and is selected from the group consisting of cyclopentanone, cyclotene, cyclotene acetate, cyclotene propionate, cyclotene butyrate, cyclotene isobutyrate, 2-geranylcyclopentanone, 2-hexylcyclopentanone, 2-hexylidene cyclopentanone, 2-cyclopentylcyclopentanone, 2-amyl-2-cyclopentenone, 3-methyl-2-pentyl-2-cyclopentenone, 3-ethyl-2-hydroxy-2-cyclopentenone, 2-hydroxy-3,4-dimethyl-2-cyclopentenone, 2-methyl-3-(2-pentenyl)-2-cyclopentenone, 3-methyl-2-(cis-2-pentenyl)-2-cyclopentenone, 3-methyl-2-(trans-2-pentenyl)-2-cyclopentenone, 3-methyl-2-cyclopentenone, 3-ethyl-2-hydroxy-4-methyl-2-cyclopentenone, 2-hexyl-2-cyclopentenone, and 2,3-dimethyl-2-cyclopentenone, and mixtures thereof.

17. The odor-modulating agent according to claim 16,
wherein the furan compound is contained in an amount of 0.8 to 3 mass % based on 100 mass % of the odor-modulating agent;
wherein the pyran compound is contained in an amount of 8 to 12 mass % based on 100 mass % of the odor-modulating agent, and
wherein the cyclopentanone derivative is contained in an amount of 0.5 to 3 mass % based on 100 mass % of the odor-modulating agent.

18. The odor-modulating agent according to claim 15, wherein the furan compound and the pyran compound have a molar ratio of 1:2 to 1:5.

19. The odor-modulating agent according to claim 1, wherein the at least one furan compound further comprises at least one member selected from the group consisting of furfural, furfuryl alcohol, 2-propionylfuran, 2-ethylfuran, menthofuran, 2-methyl-3-furanthiol, 2-methyl-3-tetrahydrofuranthiol, 2-methyl-4,5-dihydro-3-furanthiol, 2-methylfuran, 2-methyltetrahydrofuran, 2-hexanoylfuran, 2-pentylfuran, 2-propylfuran, 2-(3-phenylpropyl)tetrahydrofuran, 2,3-dihydrobenzofuran, 2,4-dimethyl-4-phenyltetrahydrofuran, 2-furfuryl-5-methylfuran, 2-heptylfuran, 2-methylbenzofuran, 2-methyl-5-propionylfuran, 2-(5-ethenyl-5-methyltetrahydrofuran-2-yl)-propanal, 3-{[2-methyl-(2 or 4), 5-dihydro-3-furil]thio}-2-methyltetrahydrofuran-3-thiol, 2-ethenyl-5-isopropenyl-2-methyltetrahydrofuran, 5-methyl-2-furanmethanethiol, 6-methyl-2,3-dihydrothieno[2,3-c]furan, 2,5-dimethoxytetrahydrofuran, 3-acetyl-2,5-dimethylfuran, 2-acetyl-5-methylfuran, 2-acetylfuran, 2-butylfuran, 2,5-diethyltetrahydrofuran, difurfuryl disulfide, difurfuryl ether, difurfuryl sulfide, and 2,5-dimethyl-3-furanthiol.

20. The odor-modulating agent according to claim 1, wherein the at least one pyran compound further comprises at least one member selected from the group consisting of maltol, 4-acetoxy-3-pentyltetrahydropyran, 3,5-dihydroxy-6-methyl-2,3-dihydro-4(4H)-pyranon, 6-ethenyl-2,2,6-trimethyltetrahydropyran, 5-methyl-3-butyltetrahydropyran-4-yl acetate, octahydro-2H-1-benzopyran-2-one, 4-methyl-2-(2-methyl-1-propenyl)tetrahydropyran, (2 S,4aR, 8aS)-2,5,5,8a-tetramethyl-3,4,4 a, 5,6, 8a-hexahydro-2H-1-benzopyran, 6-ethenyl-2,2,6-trimethyltetrahydro-3 (4H)-pyranon, and 2,6-diethyl-5 isopropyl-2-methyltetrahydro-2H-pyran.

21. An odor-modulating method comprising spraying in the air an odor-modulating agent comprising the odor-modulating agent according to claim 1, wherein the at least one oxygen-containing cyclic compound is contained in an amount of 10 to 25 mass % based on 100 mass % of the odor-modulating agent.

* * * * *